(12) United States Patent  
Greenberg et al.

(10) Patent No.: US 7,149,586 B2  
(45) Date of Patent: Dec. 12, 2006

(54) VARIABLE PITCH ELECTRODE ARRAY

(75) Inventors: Robert Greenberg, Los Angeles, CA (US); Richard Williamson, Saugus, CA (US); Mark Humayan, La Canada, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 210 days.

(21) Appl. No.: 10/112,801

(22) Filed: Mar. 28, 2002

(65) Prior Publication Data

US 2003/0187491 A1    Oct. 2, 2003

(51) Int. Cl.  
*A61N 1/00* (2006.01)
(52) U.S. Cl. .................................... 607/116
(58) Field of Classification Search ............... 600/373, 600/377, 378, 393; 607/53, 54, 116  
See application file for complete search history.

(56) References Cited

U.S. PATENT DOCUMENTS

| | | | |
|---|---|---|---|
| 3,699,970 A | 10/1972 | Brindley et al. | |
| 4,573,481 A | 3/1986 | Bullara | |
| 4,628,933 A | 12/1986 | Michelson | |
| 4,721,551 A | 1/1988 | Byers et al. | |
| 4,837,049 A | 6/1989 | Byers et al. | |
| 4,969,468 A * | 11/1990 | Byers et al. | 600/373 |
| 5,016,633 A | 5/1991 | Chow | |
| 5,024,223 A | 6/1991 | Chow | |
| 5,109,844 A | 5/1992 | de Juan, Jr. et al. | |
| 5,215,088 A | 6/1993 | Normann et al. | |
| 5,476,494 A | 12/1995 | Edell et al. | |
| 5,556,423 A | 9/1996 | Chow et al. | |
| 5,597,381 A | 1/1997 | Rizzo, III | |
| 5,668,577 A * | 9/1997 | Sutter | 345/563 |
| 5,895,415 A | 4/1999 | Chow et al. | |
| 5,935,155 A | 8/1999 | Humayun et al. | |
| 5,944,747 A | 8/1999 | Greenberg et al. | |
| 6,032,062 A | 2/2000 | Nisch | |
| 6,038,480 A | 3/2000 | Hrdlicka et al. | |
| 6,091,979 A * | 7/2000 | Madsen | 600/377 |
| 6,112,124 A * | 8/2000 | Loeb | 607/137 |
| 6,165,192 A | 12/2000 | Greenberg et al. | |
| 6,230,057 B1 | 5/2001 | Chow et al. | |
| 6,324,429 B1 | 11/2001 | Shire et al. | |
| 6,400,989 B1 | 6/2002 | Eckmiller | |
| 2002/0000238 A1 | 1/2002 | Greenberg et al. | |
| 2002/0128700 A1 * | 9/2002 | Cross | 607/117 |
| 2002/0193845 A1 * | 12/2002 | Greenberg et al. | 607/54 |
| 2004/0172099 A1 * | 9/2004 | Eckmiller et al. | 607/54 |

FOREIGN PATENT DOCUMENTS

DE    101 20 908 A 1    *    4/2001

* cited by examiner

*Primary Examiner*—Robert E. Pezzuto  
*Assistant Examiner*—Frances P. Oropeza  
(74) *Attorney, Agent, or Firm*—Scott B. Dunbar; Tomas Lendvai

(57) ABSTRACT

The present invention is an implantable electrode array having electrodes with variable pitch and variable size. Electrode arrays of the prior art provide electrodes with a common spacing and size. However, this is not how the human body is arranged. As an example, the retina has closely spaced retinal receptors near the fovea. Those receptors are spaced farther apart, farther away from the fovea. Further, the amount of electrical current required to stimulate the perception of light increases with distance from the fovea. Hence, larger electrodes are required to transfer the necessary current farther away from the fovea.

21 Claims, 3 Drawing Sheets

VARIABLE PITCH ELECTRODE ARRAY

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to electrode arrays, and more particularly to implantable electrode arrays for medical devices.

BACKGROUND OF THE INVENTION

Arrays of electrodes for neural stimulation are commonly used for a variety of purposes. Some examples include: U.S. Pat. No. 3,699,970 to Brindley describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

It is well known that the resolution of light perception on the retina is highest at the fovea, and significantly lower at the periphery of the retina. Resolution reduces gradually across the surface of the retina moving from the fovea to the periphery.

Applicant has discovered, through experimental use of a retinal prosthesis, that a very small amount of power is needed to stimulate the perception of light near the fovea; while a much larger amount of power is needed to stimulate the perception of light further from the fovea. The resolution of a retinal electrode array is limited by the size and spacing of the individual retinal electrodes. The size of a retinal electrode is limited the amount of power that must be transferred from the electrode to neural tissue, to create the perception of light. As electrode size decreases, or power increases, charge density on the electrode increases. At high charge densities, electrodes tend to corrode, or dissolve in a saline environment. Charge density is the primary limit on how small electrodes can be made and how closely that can be placed.

SUMMARY OF THE INVENTION

The present invention is an implantable electrode array having electrodes with variable pitch and variable size. Electrode arrays of the prior art provide electrodes with a common spacing and size. However, this is not how the human body is arranged. As an example, the retina has closely spaced retinal light receptors near the fovea. The light receptors are spaced farther apart, farther away from the fovea, near the periphery of the retina. Further, the amount of electrical current required to stimulate the perception of light increases with distance from the fovea. Hence, larger electrodes are required to transfer the necessary current farther away from the fovea. By placing small, closely spaced low power electrode near the fovea, and larger widely spaced electrode at the periphery, resolution is maximized.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
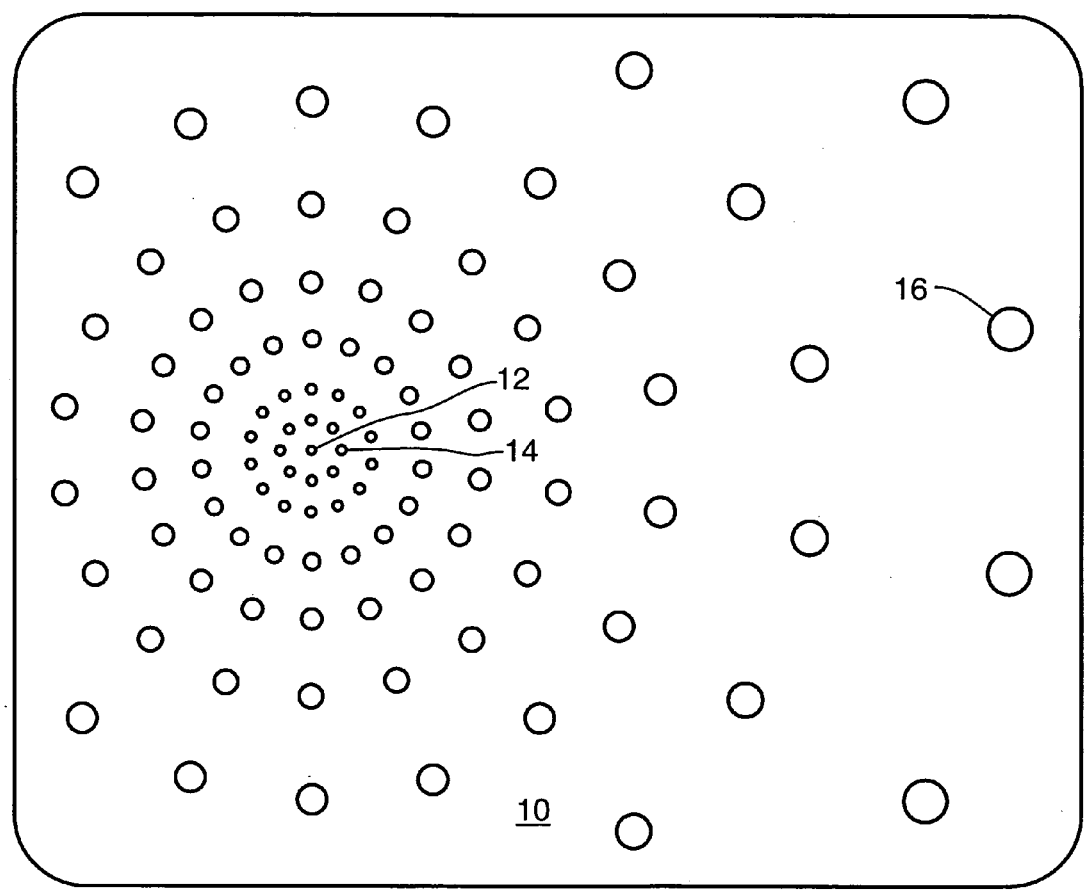
FIG. 1 is a view of the preferred retinal electrode array.

The present invention provides an array of variable pitch, variable size electrodes. FIG. 1 shows the invention applied to a retinal stimulator for artificial sight. Electrodes on the preferred retinal electrode array 10 begin very small and close together with a center electrode 12 at the fovea. A first circle of electrodes 14 approximately 10 microns in width are placed 5 microns apart. The size and pitch of the electrodes increases proportionally moving away from the fovea. It is not necessary that the fovea be at the center of the electrode array. The preferred electrode array extends further from the fovea in the direction opposite from the optic nerve (not shown), with the largest electrode 16 at the furthest point from the optic nerve. The largest electrode is 1 millimeter in width and 4 millimeters from the nearest electrode. The preferred array body is curved to match the curvature of the retina.

Figure 3:
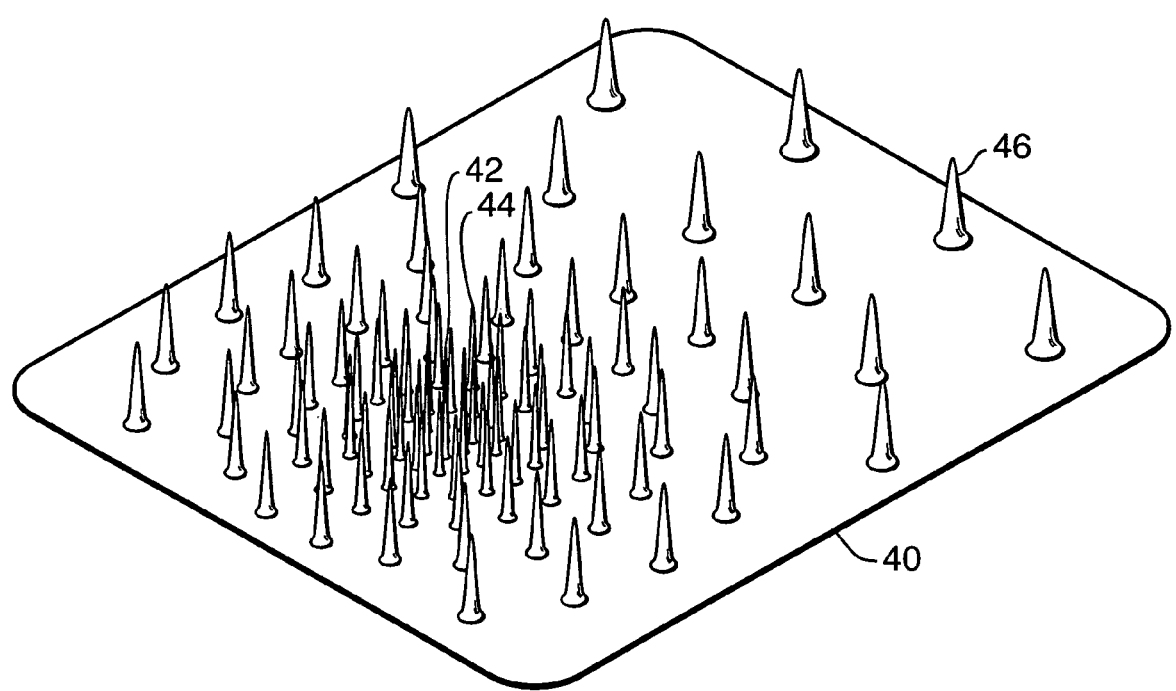
FIG. 3 is a view of an alternate electrode array used in a cortical stimulator.

It should be noted that FIG. 1 is not drawn to scale as a scale drawing would be impossible, given PTO accepted dimensions. Further, the preferred electrode array would have far more electrodes than those shown. Several different types of electrode are possible in a retinal electrode array such as spikes (as shown in FIG. 3) mushrooms or other elongated or recessed shapes. The present invention is independent of the type of electrode used. The variation of electrode size is due to limitations in the charge density supported by current electrode designs. Future electrode designs may improve charge density capability obviating the need to vary electrode size. In such a case, it would still be advantageous to vary electrode pitch.

Figure 2:
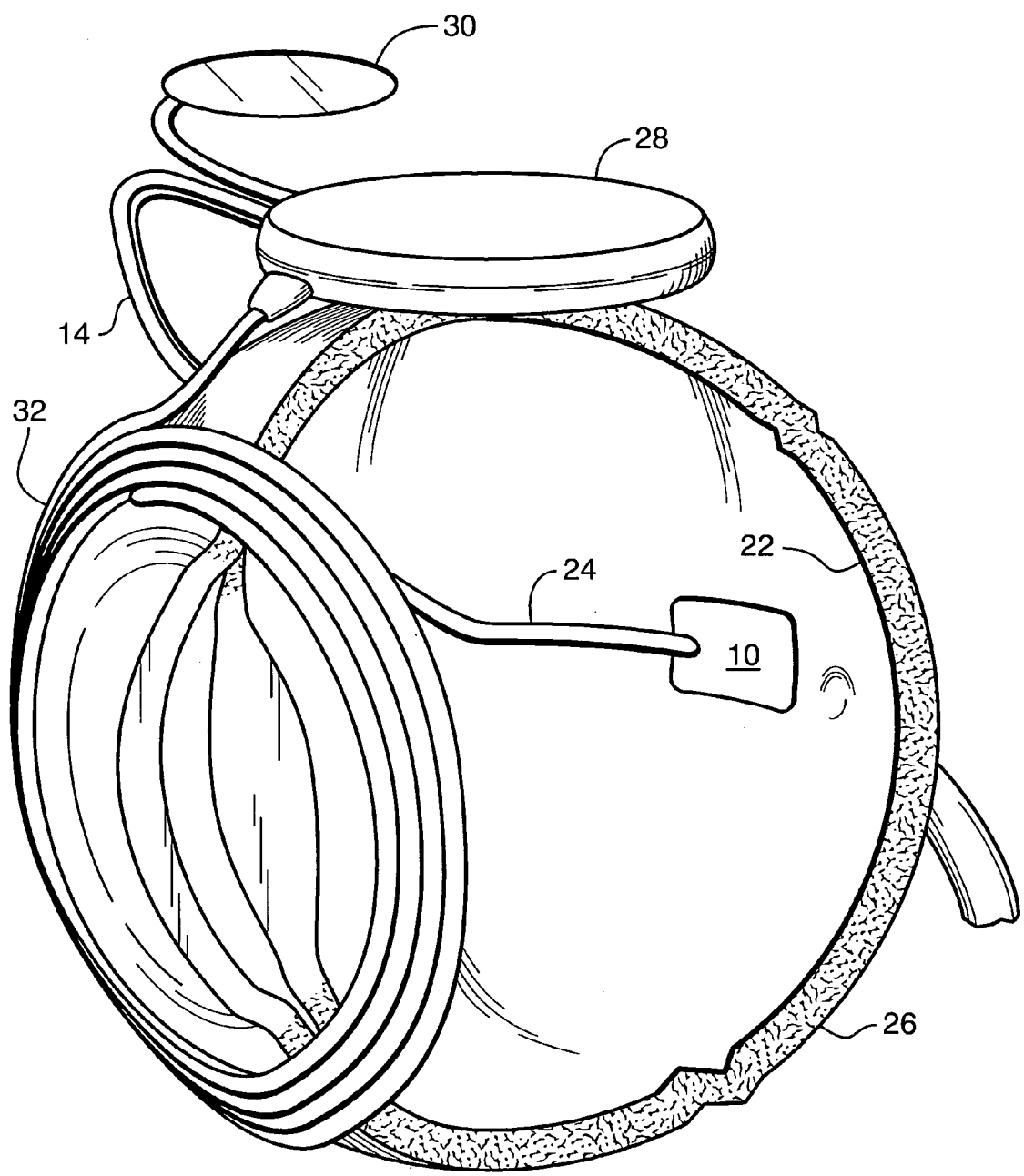
FIG. 2 is a view of the preferred retinal prosthesis.

FIG. 2 shows the preferred retinal prosthesis for use with the variable pitch electrode array of the present invention. The variable pitch electrode array 10 is placed against the outer surface of a retina 22 (epiretinally). A cable 24 pierces a sclera 26 and attaches to an electronic control unit 28. The electronic control unit is attached to the sclera and moves with the sclera. A return electrode 30 is placed outside the sclera and distant from the retina 22. Electricity travels through the body between the stimulating electrode array 10 and return electrode 30, to complete an electrical circuit.

The retinal prosthesis also includes a coil 32 around the front of the sclera and coupled to the electronic control unit 28. The coil 32 receives an inductive signal from an external unit (not shown). The signal includes the video information provided to the stimulating electrode array 10.

The present invention is not limited to the retina, but is applicable to may parts of the human body as show in the alternate embodiment of FIG. 3.

FIG. 3 shows an alternate embodiment of the invention applied to a cortical brain stimulator. In a cortical brain stimulator, the electrode must pierce the cerebral cortex. Hence spike electrodes are used. Spike electrodes on the cortical electrode array 40 begin very small and close together with a center electrode 42 at the center of the visual "area" of the cerebral cortex. A first circle of electrodes 44 approximately 5 microns in width are placed 2.5 microns apart. The size and pitch of the electrodes increase proportionally moving away from the center of the visual portion of the cortex. It is not necessary that the center of the visual portion of the cortex be at the center of the electrode array. The furthest electrode 46 is also the largest. Charge density is less of an issue in cortical stimulation than in retinal stimulation. Hence an array that varies electrode pitch without varying electrode size could be quite effective.

Accordingly, what has been shown is an improved electrode array for neural stimulation with electrodes of variable pitch and variable size. While the invention has been described by means of specific embodiments and applications thereof, it is understood that numerous modifications and variations could be made thereto by those skilled in the art without departing from the spirit and scope of the invention. For example, while it is preferable to vary both pitch and size, varying only pitch will have advantageous results. It is therefore to be understood that within the scope of the claims, the invention may be practiced otherwise than as specifically described herein.

What is claimed is:

1. An implantable electrode array for visual stimulation comprising:
   an array body;
   a plurality of electrodes spaced across said array body at varying intervals, the intervals increasing continuously and proportionally from a central portion of said array body to an outer edge of said array body,
   wherein said intervals are smaller toward said central portion of said array body and increasing toward said outer edge of said array body.

2. The implantable electrode array according to claim 1, wherein said electrodes are of varying size.

3. The implantable electrode array according to claim 2, wherein varying size of said electrodes is smaller toward said central portion of said array body, and increasing toward the outer edge of said array body.

4. The implantable electrode array according to claim 1, wherein said varying intervals of said electrodes increase proportionally to a distance from said central portion.

5. The implantable electrode array according to claim 3, wherein said varying size of said electrodes increases proportionally to a distance from said central portion.

6. The implantable electrode array according to claim 1, wherein said electrodes are elongated electrodes.

7. The implantable electrode array according to claim 6, wherein said elongated electrodes are mushroom shaped electrodes.

8. The implantable electrode array according to claim 6, wherein said elongated electrodes are spike electrodes.

9. The implantable electrode array according to claim 6, wherein said elongated electrodes are of varying size.

10. The implantable electrode array according to claim 3, wherein said electrodes are elongated electrodes.

11. The implantable electrode array according to claim 4, wherein said electrodes are elongated electrodes.

12. The implantable electrode array according to claim 5, wherein said electrodes are elongated electrodes.

13. An implantable retinal electrode array comprising:
    an array body, suitable to be implanted adjacent to a retina near its fovea;
    a plurality of electrodes spaced across said array body at varying intervals the intervals increasing continuously and proportionally from a central portion of said array body to an outer edge of said array body,
    wherein said intervals are smaller toward said central portion of said array body and increasing toward said outer edge of said array body.

14. The implantable retinal electrode array according to claim 13, wherein said electrodes are of varying size.

15. The implantable retinal electrode array according to claim 14, wherein said varying size of said electrode is smaller toward the fovea and increasing toward the outer edge of the retina.

16. The implantable retinal electrode array according to claim 15, wherein said varying intervals of said electrodes increase proportionally to a distance from the fovea.

17. The implantable retinal electrode array according to claim 15, wherein said varying size of said electrodes increases proportionally to a distance from the fovea.

18. An implantable cortical electrode array comprising:
    an array body;
    a plurality of spike electrodes of varying size spaced across said array body at varying intervals the intervals increasing continuously and proportionally from a central portion of said array body to an outer edge of said array body, wherein said intervals, are smaller toward said central portion of said array body and increasing toward said outer edge of said array body.

19. The implantable electrode array according to claim 18, wherein said varying size of said spike electrodes is smaller toward said central portion of said array body, and increasing toward an outer edge of said array body.

20. The implantable electrode array according to claim 19, wherein said varying intervals of said spike electrodes increase proportionally to a distance from said central portion.

21. The implantable electrode array according to claim 20, wherein said varying size of said spike electrodes increases proportionally to a distance from said central portion.

* * * * *

UNITED STATES PATENT AND TRADEMARK OFFICE
CERTIFICATE OF CORRECTION

PATENT NO. : 7,149,586 B2 Page 1 of 1
APPLICATION NO. : 10/112801
DATED : December 12, 2006
INVENTOR(S) : Robert J. Greenberg, Richard Williamson and Mark Humayun It is certified that error appears in the above-identified patent and that said Letters Patent is hereby corrected as shown below:

On the Title Page, Item (75) please delete "Humayan, Mark" and insert -- Humayun, Mark --.

Signed and Sealed this

Seventh Day of August, 2007

JON W. DUDAS
*Director of the United States Patent and Trademark Office*